United States Patent [19]
Curley

[11] Patent Number: 5,788,636
[45] Date of Patent: Aug. 4, 1998

[54] METHOD AND SYSTEM FOR FORMING AN ULTRASOUND IMAGE OF A TISSUE WHILE SIMULTANEOUSLY ABLATING THE TISSUE

[75] Inventor: Michael G. Curley, Cambridge, Mass.

[73] Assignee: Acuson Corporation, Mountain View, Calif.

[21] Appl. No.: 805,473

[22] Filed: Feb. 25, 1997

[51] Int. Cl.$^6$ ........................................................ A61B 8/00
[52] U.S. Cl. ................................................ 600/439; 606/31
[58] Field of Search ............................ 128/653.1, 660.03; 606/31, 34, 37–38, 41, 45–46; 607/98–101; 601/2, 3; 600/439

[56] References Cited

U.S. PATENT DOCUMENTS

| | | | |
|---|---|---|---|
| 4,517,976 | 5/1985 | Murakoshi et al. | 606/46 |
| 4,658,828 | 4/1987 | Dory | 128/660.03 |
| 4,936,281 | 6/1990 | Stasz . | |
| 5,143,074 | 9/1992 | Dory . | |
| 5,183,048 | 2/1993 | Eberle . | |
| 5,279,299 | 1/1994 | Imran . | |
| 5,324,284 | 6/1994 | Imran . | |
| 5,385,148 | 1/1995 | Lesh et al. . | |
| 5,409,000 | 4/1995 | Imran . | |
| 5,429,136 | 7/1995 | Milo et al. . | |
| 5,435,304 | 7/1995 | Oppelt et al. . | |
| 5,454,370 | 10/1995 | Avitall . | |
| 5,454,809 | 10/1995 | Janssen . | |
| 5,526,815 | 6/1996 | Granz et al. | 128/660.03 |
| 5,588,432 | 12/1996 | Crowley . | |
| 5,657,755 | 8/1997 | Desai | 606/41 |

OTHER PUBLICATIONS

"Ultrasound Cardioscopy: Embarking on a New Journey", Seward, et al., Mayo Clinic Proceedings, Jul. 1996, vol. 71 No. 7, pp. 629–635.

"Thermal Dose Determination In Cancer Therapy", S.A. Sapareto and W.C. Dewey, International Journal of Radiology, Oncology, Biology, and Physics 10(6): 787–800 Jun. 1984.

"Biophysics and Pathology of Catheter Energy Delivery Systems", Nath & Haines, Progress in Cardiovascular Diseases, Jan./Feb. 1995, vol. XXXVII, No. 4, pp. 185–204.

"Radiofrequency Tissue Ablation: Increased Lesion Diameter with a Perfusion Electrode", Goldberg et al., Acad Radiol Aug. 1996; 3:636–644.

*Primary Examiner*—Francis Jaworski
*Attorney, Agent, or Firm*—Brinks Hofer Gilson & Lione

[57] ABSTRACT

A method and system for forming an ultrasound image of a tissue while simultaneously ablating the tissue in which the application of therapy current is sequenced with at least the ultrasonic detection phase of the ultrasonic visualization process. In this way, no ultrasonic detection takes place while therapy current passes, and no therapy current passes while ultrasonic detection takes place. The sequencing can take place using a communication protocol between a therapy system controlling the application of therapy current and an ultrasonic imaging system controlling the ultrasonic visualization process. Depending on the communication protocol used, the therapy system and the ultrasonic imaging system can handoff control to one another or one system can have exclusive control over the other.

35 Claims, 3 Drawing Sheets

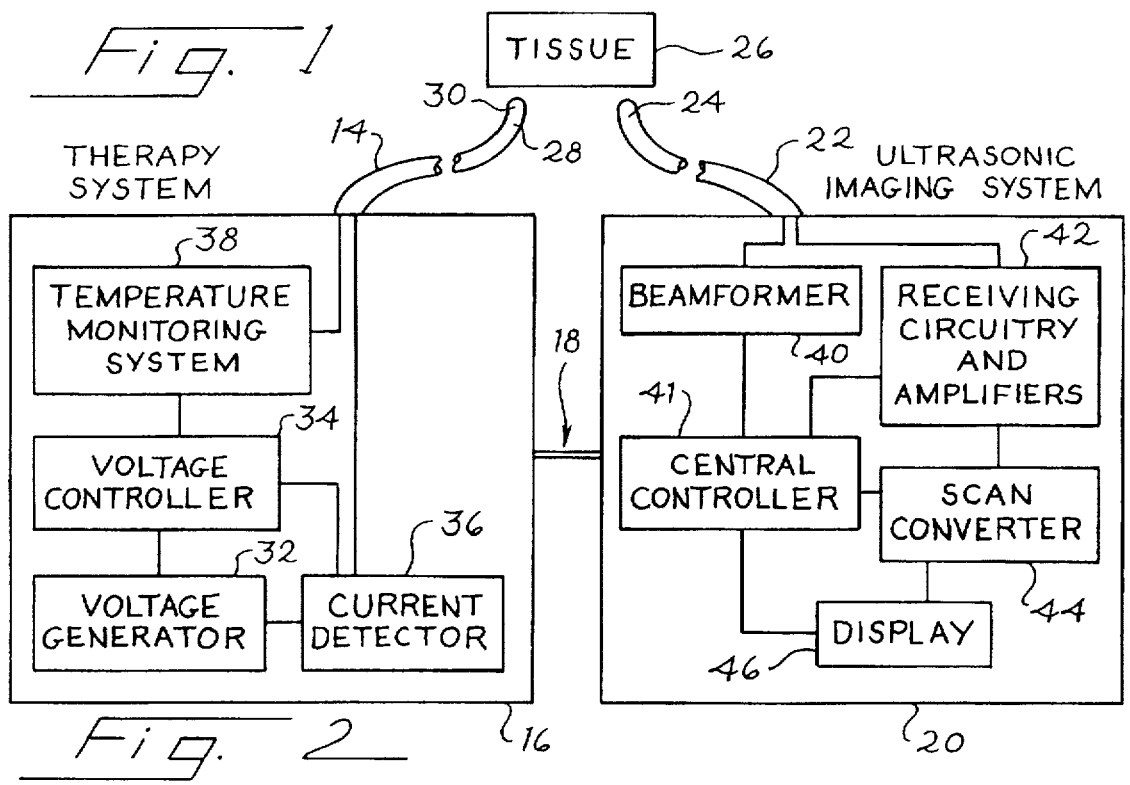
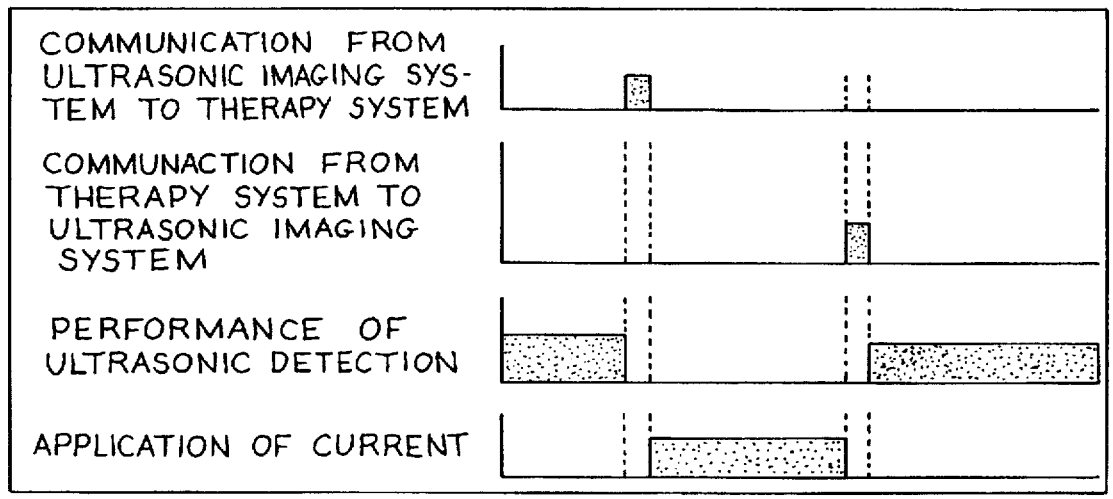
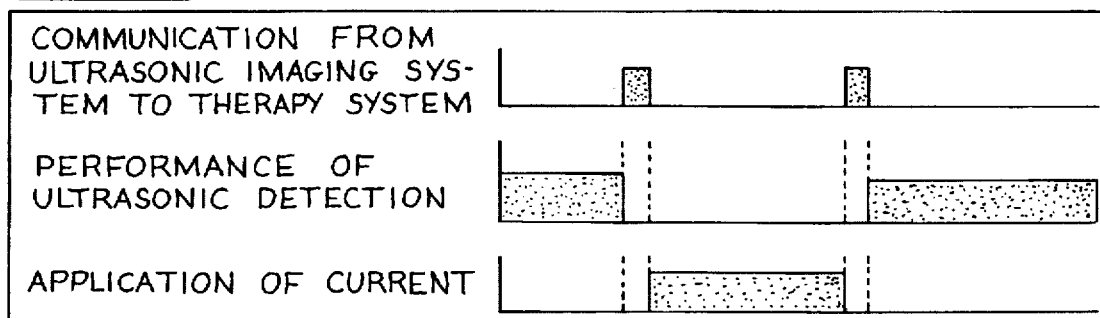

5,788,636

METHOD AND SYSTEM FOR FORMING AN ULTRASOUND IMAGE OF A TISSUE WHILE SIMULTANEOUSLY ABLATING THE TISSUE

BACKGROUND OF THE INVENTION

Radiofrequency energy can be applied to tissue in order to heat and thereby affect the tissue. This most often results in a region of necrotic or ablated tissue. Such a therapy is, for example, applied to the ablation of liver cancer, as described in "Radiofrequency Tissue Ablation: Increased Lesion Diameter with a Perfusion Electrode," by S. N. Goldberg, G. S. Gazelle, L. Solbiati, W. J. Rittman, and P. R. Mueller, published in *Academic Radiology*, 3(8):636–44. It is also applied to the ablation of myocardium when the patient is suffering from tachycardia, as described in "Biophysics and Pathology of Catheter Energy Delivery Systems," by S. Nath and D. E. Haines, published in Progress in *Cardiovascular Diseases*, 37(4):185–204.

This therapy is performed by passing a high-frequency (typically 200–500 kHz), high-amplitude (typically 0.5–1 A) electrical current through the tissue to be ablated. The therapy current is generated by placing one or more metal therapy electrodes against the tissue to be ablated. When a single therapy electrode is used, therapy current is passed from this electrode into the tissue and then to a larger counter electrode contacting the tissue elsewhere. When more than one therapy electrode is used, the therapy current can be passed between these electrodes through the tissue. Ionic transport carries the current within the tissue and generates heat proportional to the square of the local current density. The maximum heating and the maximum temperature rise occur adjacent to the therapy electrode(s). This temperature rise will, if maintained for a sufficient time, alter the function of or kill the tissue. A description of the relationship between tissue temperature and the time required to cause thermal damage can be found in "Thermal Dose Determination in Cancer Therapy," by S. A. Sapareto and W. C. Dewey, published in *International Journal of Radiation Oncology, Biology and Physics*, 10(6):787–800.

Ultrasound can be used to guide radiofrequency ablation therapies. Because the location of the regions to be treated either can be identified by ultrasound (often the case with liver tumors) or can be indicated by or referenced to known anatomic references (as in the case of cardiac ablation), ultrasound is increasingly being used in conjunction with ablation procedures to guide the placement of the therapy devices. Further, as heating tissue to therapeutic temperatures alters the echogenic nature of the tissue, ultrasound is now also being used to monitor the growth of the treated region. A description of ultrasound's role in cardiac radiofrequency ablation can be found in "Ultrasound Cardioscopy: Embarking on a New Journey," by J. B. Seward, D. L. Packer, R. C. Chan, M. G. Curley, and A. J. Tajik, published in *Mayo Clinic Proceedings*, 71(7) (1996).

Monitoring tissue using ultrasound while simultaneously applying therapeutic current is often complicated by the electrical interference that the high-amplitude, high-frequency therapy current causes on the ultrasound image during the ultrasonic detection phase of the visualization process. While this interference can be reduced through improved shielding of the electrical conductors within the ultrasound transducer or through improved signal processing within the ultrasonic imaging system, such improvements can add to the size of the transducer or can add to the cost of the transducer or system.

SUMMARY OF THE INVENTION

The present invention is directed to a method and system for forming an ultrasound image of a tissue while simultaneously ablating the tissue. According to this invention, the application of therapy current is sequenced with the performance of ultrasonic detection, resulting in essentially simultaneous application of current and ultrasonic detection. This avoids electrical interference on the ultrasound image caused by the radiofrequency therapy current without adding to the size of the transducer or to the cost of the transducer or system.

Other aspects of this invention relate to the communication protocols that allow the system to perform ultrasonic detection while simultaneously ablating the tissue.

BRIEF DESCRIPTION OF THE DRAWINGS

FIG. 1 is a block diagram of a preferred embodiment of a system of the present invention.

FIG. 2 is an illustration of a communication protocol of a second preferred embodiment.

FIG. 3 is an illustration of a communication protocol of a third preferred embodiment.

DETAILED DESCRIPTION OF THE PRESENTLY PREFERRED EMBODIMENTS

Figure 4:
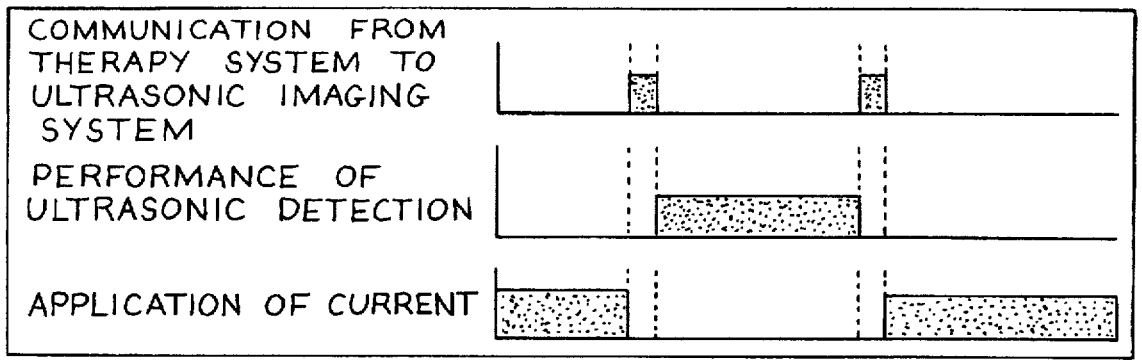
FIG. 4 is an illustration of a communication protocol of a fourth preferred embodiment.

Turning now to the drawings, FIG. 1 illustrates the components that can be used in the preferred embodiments described below. A therapeutic delivery device 14 contains a therapeutic electrode 28 and a temperature sensor 30. The therapeutic delivery device 14 connects to a therapy system 16, which contains a voltage generator 32 responsive to a voltage controller 34 and coupled to a current detector 36. The therapy system 16 also contains a temperature monitoring system 38 coupled to the voltage controller 34 and responsive to the temperature sensor 30. As used herein, one component can be "responsive" or "coupled" to another component either directly (as when two components are connected by a conductor) or indirectly (as when there is intermediate signal processing between two components).

A communication link 18 connects the therapy system 16 to an ultrasonic imaging system 20.

The ultrasonic imaging system 20 includes a central controller 41, a beam former 40 responsive to the central controller 41, and receiving circuitry and amplifiers 42 responsive to the central controller 41. The receiving circuitry and amplifiers 42 are coupled to a scan converter 44, which is coupled to a display 46. The imaging system 20 attaches to an ultrasound delivery device 22 containing an ultrasound transducer 24 responsive to the beam former 40 and coupled to the receiving circuitry and amplifiers 42. The function of these components will be described below.

The voltage generator 32 in the therapy system 16 generates a voltage and sends the resulting current to the therapy electrode 28. The voltage controller 34 sets the frequency and amplitude of the voltage produced by the generator 32, as well as its sequencing in time. The voltage controller 34 makes this determination based on information received from the user via an input interface or from the temperature monitoring system 38 and the current detector 36. The temperature monitoring system 38 receives thermal information from the temperature sensor 30 in the therapeutic delivery device 14, while the current detector 36 determines the amount of current sent to the therapy electrode 28.

The current flowing from the therapy system 16 to the therapy electrode 28 passes to the tissue 26 when the electrode 28 is placed adjacent to the tissue 26. This current spreads as it penetrates into the tissue 26 and propagates either to a second therapy electrode or to a distant, larger counter electrode (not shown). As it passes through the tissue 26, the current generates heat according to the local current density, ablating (i.e., causing thermal damage to) the tissue 26. As used herein, the term "ablation" refers to the process that affects the tissue by thermal means.

The communication link 18 connects the therapy system 16 to the ultrasonic imaging system 20 and is capable of sending signals between the two systems 16, 20.

The ultrasonic imaging system 20 controls the time during which the ultrasound transducer 24 is performing ultrasonic visualization of the tissue 26. The imaging system 20 allows the user to adjust parameters which affect the time needed for ultrasonic visualization. As is well known in the art, these parameters include, but are not limited to, image depth, image width, and frame-rate, the number of frames per second that will be displayed to the user. The central controller 41 interprets the set-up information entered by the user and configures the other components of the ultrasonic imaging system 20 accordingly. As used herein, the term "ultrasonic visualization" refers to the well-known interrogating-and-imaging process which includes ultrasound generation, ultrasonic detection, image reconstruction, and image presentation phases.

During the ultrasound generation phase, the beam former 40 applies a voltage to the transducer 24 to cause it to vibrate and emit ultrasonic energy. Next, in the ultrasonic detection phase, the receiving circuitry 42 measures the voltages created by the transducer 24 when ultrasonic energy reflected by the structures in the tissue 26 impinge on the transducer 24, creating a scan line. Additional ultrasonic energy is transmitted and received until enough scan lines are formed to create a frame. At that point, the image reconstruction phase begins. During this phase, the scan converter 44 processes the amplified, sensed voltages to create an image of the tissue 26. Finally, the display 46 presents the image to the user during the presentation phase. In a cardiac ablation application, for example, the desired frame-rate is usually 10–60 frames per second. Accordingly, the image is presented to the user in $\frac{1}{60}$ to $\frac{1}{60}$ of a second.

Prior to a description of the preferred embodiments, it is important to understand that the therapy current need not be applied throughout the entire ablation process. That is, continuous ablation of the tissue (i.e., continuous thermal damage to the tissue) will be maintained even if the therapy current is interrupted during the ablation process. Therapy current can be interrupted without significant effect on tissue heating if the resulting time-averaged current is sufficient to cause heating to therapeutic temperatures. This can be achieved by increasing the magnitude of the therapy current during its application or by increasing the duration of the ablation process to compensate for the interruption in therapy current. See S. A. Sapareto and W. C. Dewey, supra. If a sufficient amount of heat is generated within the tissue 26 before the therapy current is interrupted, ablation of the tissue 26 will continue even though therapy current is momentarily interrupted.

It is preferable that the time the therapy current is off is short compared to the natural decay time of the heating field. This time scale is approximately equal to the length scale of the heating field squared divided by the thermal diffusivity of tissue, or $$\tau = L^2/\alpha.$$

where L is the length scale of the heating field, $\tau$ is the approximate time scale for cooling, and $\alpha$ is the thermal diffusivity of tissue, typically $1.5 \times 10^{-3}$ cm$^2$/sec.

For the shortest time scale, consider the smallest heating field—that obtained when the therapy current is first turned on. For the typical 4 mm electrode, the length scale can be taken as the diameter of the electrode, and so the time scale for cooling is about 106 seconds. Therefore, as long as the interruption of therapy current to the heating field is significantly less than 100 seconds and as long as the therapy current is increased during the "on" periods to compensate for the brief loss of heating energy, ablation of the tissue 26 will continue even though therapy current is interrupted. Instead of increasing the therapy current, the duration of the ablation process can be increased to compensate for the slight diminution in temperature resulting from the brief pauses in the application of the therapy current, if the resulting time-averaged current is sufficient to cause heating to therapeutic temperatures.

This temporal averaging of the therapeutic heating, along with the above-described components of FIG. 1, may be used in a method and system for forming an ultrasound image of a tissue while simultaneously ablating the tissue, as will be illustrated below.

FIRST PREFERRED EMBODIMENT

Ultrasonic detection can be performed simultaneously with the ablation of tissue 26 if the application of therapy current is sequenced with ultrasonic detection. With this approach, no ultrasonic detection takes place while therapy current passes, and no therapy current passes while ultrasonic detection takes place. By sequencing these steps, the application of therapy current occurs virtually simultaneously with the performance of ultrasonic detection.

First, a sufficient amount of therapy current is applied to the tissue 26 to generate enough heat for ablation to continue during an interruption in therapy current, as can be detected by the temperature sensor 30 and the temperature monitoring system 38. Next, ultrasonic detection is performed by the ultrasonic imaging system 20 during an interruption in the application of the therapy current. When detection is complete, the cycle begins again, and therapy current is reapplied to the tissue 26, as before, to generate enough heat for continuous ablation.

This method allows the tissue 26 to be ultrasonically monitored while being simultaneously ablated without the previously mentioned problem of electrical interference on the ultrasound image. When ultrasonic detection occurs in this method, no therapy current is flowing to the tissue (hence, no interference), yet the tissue is being ablated (from the heat built up before the therapy current was interrupted). Unlike other solutions to the interference problem, this solution does not significantly add to the size or cost of the transducer 24.

Sequencing may be implemented with a communication protocol, as described below, to determine when therapy current should be applied and when ultrasonic detection should be performed. Alternatively, each system 16, 20 can use information entered by a user to determine when therapy current should be applied and when ultrasonic detection should be performed, without the use of a communication protocol between the systems 16, 20.

SECOND PREFERRED EMBODIMENT

FIG. 2 illustrates the communication protocol used in the method of the second preferred embodiment. In this method, both the ultrasonic imaging system 20 and the therapy system 16 signal each other, via the communication link 18, when done performing their functions. With this "handshake" protocol, control is passed between the two systems 16, 20. Once one system indicates that it is done with its function, it cannot proceed until it receives a signal from the other system signaling that the other system is done.

The ultrasonic imaging system 20 begins performing ultrasonic detection. When detection is complete, the ultrasonic imaging system 20 stops performing ultrasonic detection and signals the therapy system 16 that it is done with its function.

Next, the therapy system 16 begins to apply therapy current to the tissue 26. When it is appropriate to interrupt the application of therapy current, the therapy system 16 stops applying the therapy current to the tissue 26 and signals the ultrasonic imaging system 20 that it is done with its function. This would occur, for example, when a sufficient amount of heat is generated within the tissue 26 to continue ablation during the time when the therapy current is interrupted, as can be detected by the temperature sensor 30 and the temperature monitoring system 38. Ultrasonic detection of the tissue 26 resumes after the ultrasonic imaging system 20 receives the signal from the therapy system 16.

THIRD PREFERRED EMBODIMENT

FIG. 3 illustrates the communication protocol used in the method of the third preferred embodiment. In the method using this protocol, the ultrasonic imaging system 20 retains exclusive control over when therapy current should be applied and when detection should be performed.

The ultrasonic imaging system 20 begins performing ultrasonic detection. When detection is complete, the ultrasonic imaging system 20 stops performing ultrasonic detection and signals the therapy system 16 that therapy current may be applied.

Next, the therapy system 16 begins to apply therapy current to the tissue 26. When the ultrasonic imaging system 20 determines that a new ultrasound image needs to be formed, it sends a signal to the therapy system 16 to indicate that the therapy current should be turned off. This determination can be based on a minimum frame-rate entered by the user. For example, in cardiac ablation applications, the minimum frame-rate is usually 10–60 frames per second. The application of therapy current is then interrupted, and ultrasonic detection is performed.

The method using this protocol can be used, for example, when careful monitoring of the growth of the treated tissue 26 is considered important. By retaining exclusive control, the ultrasonic imaging system 20 ensures that the imaging is sufficiently continuous for tracking the growth of a lesion.

FOURTH PREFERRED EMBODIMENT

FIG. 4 illustrates the communication protocol used in the method of the fourth preferred embodiment. In the method using this protocol, the therapy system 16 retains exclusive control by determining when ultrasonic detection should begin and end. This protocol can be used to ensure a particular therapy current delivery.

The therapy system 16 begins applying therapy current to the tissue 26. When it is appropriate, the therapy system 16 interrupts the application of therapy current to the tissue 26 and signals the ultrasonic imaging system 20 that detection may be performed. This would occur, for example, when a sufficient amount of heat is generated within the tissue 26 for ablation to continue during the time when the therapy current is interrupted, as can be detected by the temperature sensor 30 and the temperature monitoring system 38.

Next, the ultrasonic imaging system 20 performs ultrasonic detection. When the therapy system 16 determines that therapy current needs to be applied to the tissue 26, it sends a signal to the ultrasonic imaging system 20 to interrupt ultrasonic detection. This would happen, for example, when more therapy current is needed to generate additional heat to maintain a continued ablation of the tissue 26. Ultrasonic detection is then interrupted, and therapy current is applied to the tissue 26. This protocol, however, may produce a sub-optimal result given the complexity of the detection of ultrasound and given the delay needed for the ultrasound waves to travel into and return from the tissue 26. That is, the detection may not be complete when the therapy system 16 determines that detection must be interrupted and therapy current must be applied.

Figure 5:
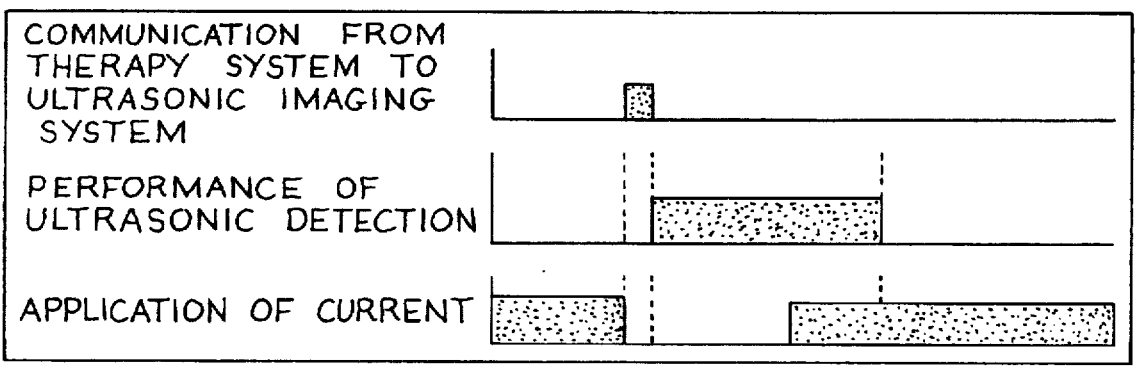
FIG. 5 is an illustration of an alternative communication protocol of the fourth preferred embodiment.

Instead of sending a signal to the ultrasonic imaging system 20 to indicate that the ultrasonic detection should be interrupted, the therapy system 16 can apply current while the detection phase continues (see FIG. 5). Although there will be interference on the image caused by the simultaneous application of current and detection, this alternative allows the user to receive an image, even though it is of lesser quality.

Figure 6:
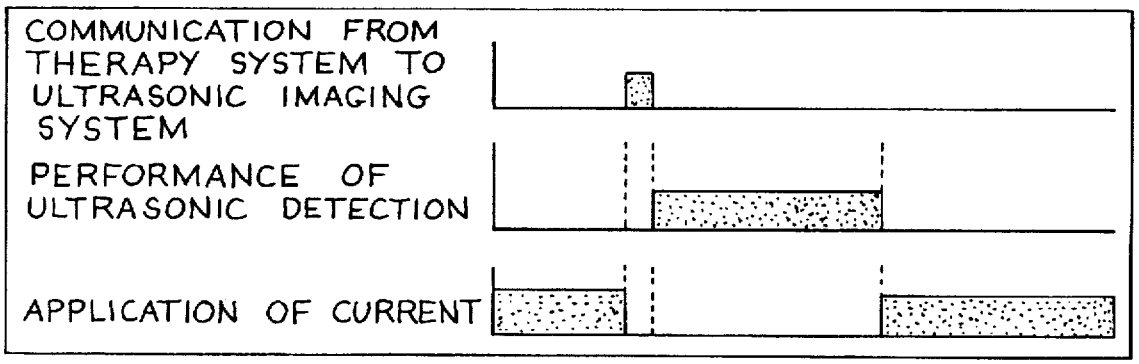
FIG. 6 is an illustration of another alternative communication protocol of the fourth preferred embodiment.

To avoid a sub-optimal result, an alternative embodiment can be used in which instead of sending two signals (one indicating that detection should begin and one indicating that it should be interrupted), the therapy system 16 sends only one signal, as shown in FIG. 6. This single signal gives the ultrasonic imaging system 20 a preset time interval to complete detection. The ultrasonic imaging system 20 would then adjust imaging parameters (including, but not limited to, image depth and width) to ensure that detection is complete in the given amount of time. At the expiration of the preset time interval, the detection phase would be complete and therapy current would be applied automatically, without the need to send a second signal from the therapy system 16 to the ultrasonic imaging system 20.

ALTERNATIVES

In the preferred embodiments described above, the application of therapy current is sequenced with the performance of the ultrasonic detection because it is during the detection phase that the ultrasound system 20 is most susceptible to noise. The other phases of the ultrasonic visualization process (i.e., ultrasound generation, image reconstruction, and image presentation) can be performed while the therapy system 16 applies current. Alternatively, the application of therapy current can be interrupted throughout the entire ultrasonic visualization process. This can be done for simplicity since the detection phase can consume the largest fraction of time for the entire ultrasonic visualization process.

Ultrasound delivery devices include all types of devices that contain a transducer. These devices include, but are not limited to, transthoracic, transabdominal, transesophageal, endorectal, endovaginal, and transluminal surgical devices and catheters. Therapy delivery devices include several devices that contain an electrode. For example, in cardiac applications, the therapy electrodes can be delivered using a catheter, while for liver tumor applications, the therapy electrodes can be delivered using a catheter or a needle. Additionally, the therapy electrode can be a separate device delivered through an introducer needle or sheath.

The ultrasound transducer can be of any type (e.g., mechanical array, ultrasound array, synthesized B-mode) as long as the ultrasonic imaging system 20 has the ability to control the time during which ultrasound energy is being generated or detected. While the ultrasonic imaging system can have duplicate receivers and amplifiers, it can also have a single receiver and amplifier.

In any of the above protocols, an additional communication may be sent from the ultrasonic imaging system 20 to the therapy system 16. The ultrasonic imaging system 20 may communicate its duty cycle to the therapy system 16. As used herein, the duty cycle comprises the amount of time required for ultrasonic detection (or for completion of the entire ultrasonic visualization process) and the frame-rate. The time required for detection (or visualization) allows the therapy system 16 to know how long it must be off, while the frame-rate allows the therapy system 16 to know how long it can be on before another image needs to be generated. The voltage controller 34 may then alter the intensity of therapy current or increase the duration of the ablation process accordingly to ensure that the time-average of the square of the therapy current, as determined by the current detector 36, is sufficient to generate enough heat for continuous ablation of the tissue 26. As a result of the duration of the ablation process increasing, the number of times that the application of current and the performance of ultrasonic visualization (or detection) are sequenced is increased. The additional communication can be sent directly between the systems 16, 20, or it can be manually entered by the operator.

Alternatively, the current detector 36 can monitor the time-average of the square of the therapy current it is generating, and the voltage controller 34 can adjust the therapy current in real-time to maintain a particular value. Additionally, the voltage controller 34 can increase the duration of the ablation process. A combination of the therapy current-control alternatives described above can also be used. As mentioned earlier, the number of times that the application of current and the performance of ultrasonic visualization (or detection) are sequenced is increased as a result of the duration of the ablation process increasing.

The temperature of the tissue can be monitored by the temperature sensor 30 and the temperature monitoring system 38. With this information the voltage controller 34 or the user can increase the duration of the ablation process, instead of increasing the magnitude of the current, to ensure continuous ablation.

It should be noted that the temperature sensor 30 and the temperature monitoring system 38 are not strictly needed. For example, a user can use his experience to set the voltage or current level based on the electrode and tissue type.

It should be noted that the sequencing described in the embodiments can begin with either application of therapy current or ultrasonic detection.

While the above preferred embodiments show the ultrasound delivery device 22 and ultrasonic imaging system 20 as being separate components, it should be understood that they may be combined into one component. This is also true for the therapy delivery device 14 and the therapy system 16.

Figure 7:
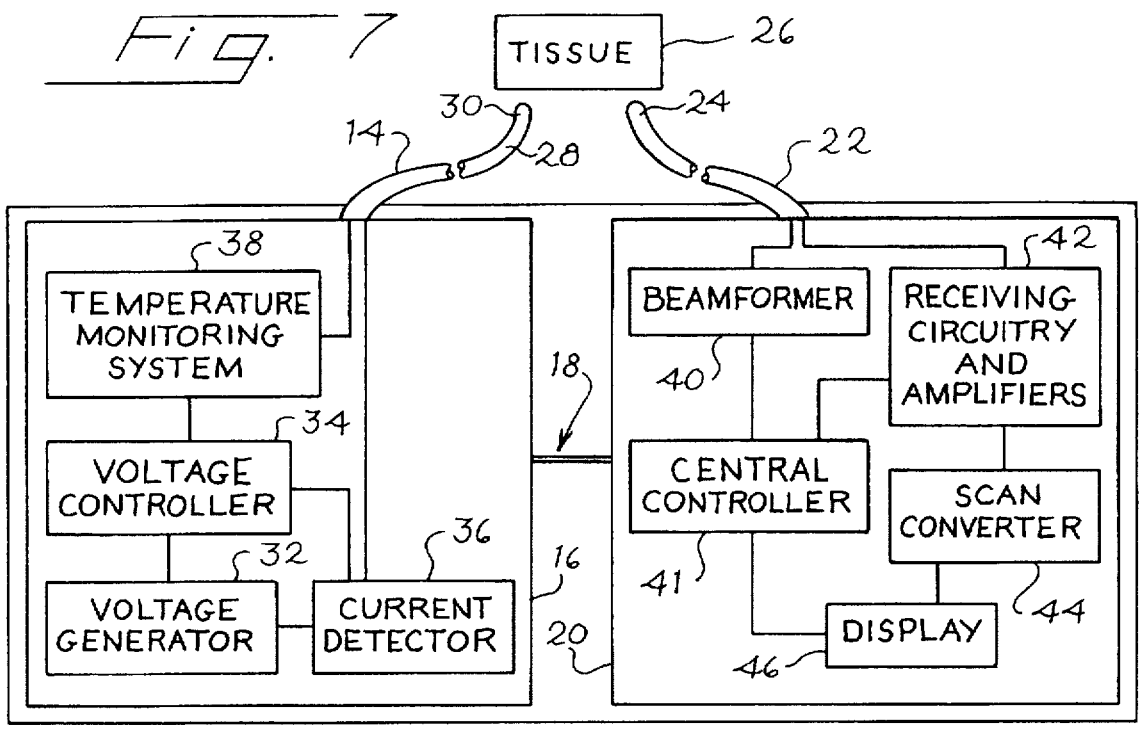
FIG. 7 is a block diagram of an alternative embodiment of the system of FIG. 1.
Figure 8:
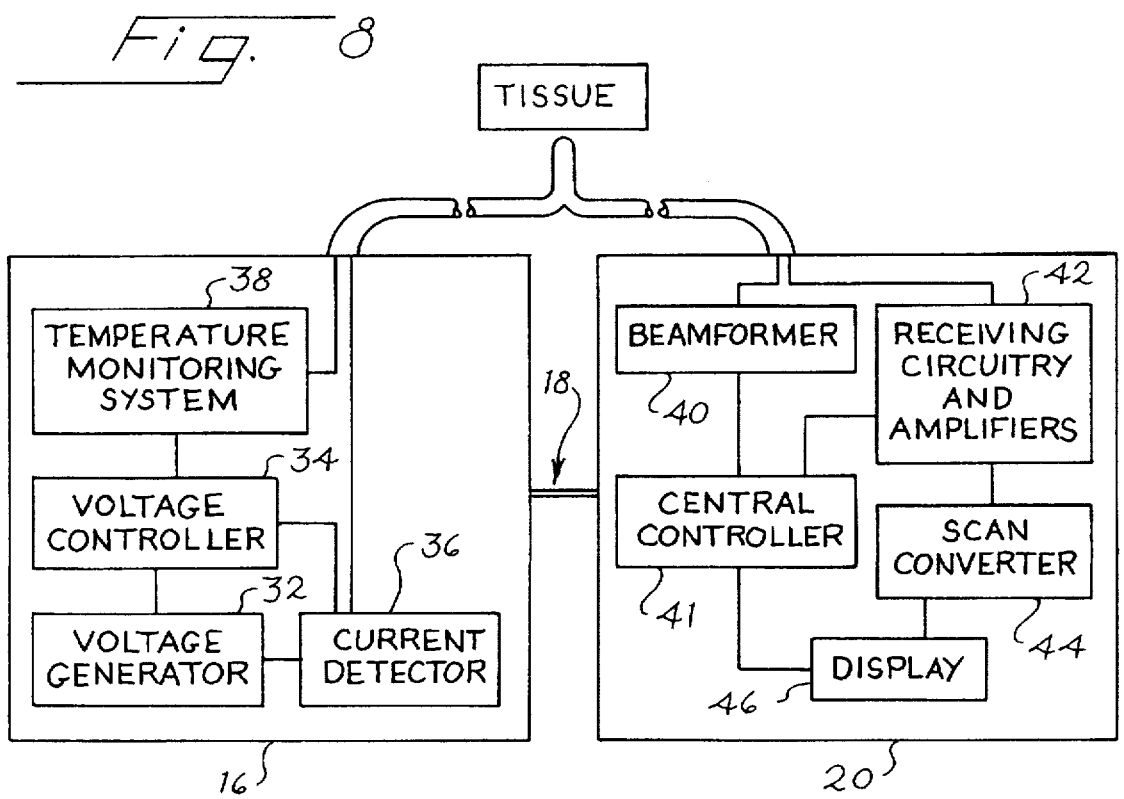
FIG. 8 is a block diagram of another alternative embodiment of the system of FIG. 1.

Also, while the above preferred embodiments show the therapy system 16 and the ultrasonic imaging system 20 as being separate components, it should be understood that they may be subsystems of an integrated therapy/visualization system (See FIG. 7). Additionally, while two separate delivery devices 14, 22 are described above, a single delivery device can house the therapy electrode 28, the ultrasound transducer 24, and the temperature sensor 30 (See FIG. 8).

The communication between the systems 16, 20 can use conventional digital communication techniques—a short period of a high voltage to communicate that control is being passed. Other, possibly more sophisticated, communication modalities can also be used.

The term "communications link" is meant in its broadest sense to be any suitable communication technology and can include, but is not limited to, communication by wire, fiber optics, and radio waves, and it can be effected using either hardware or software.

The communication protocols of the above embodiments and alternatives need not be maintained throughout a particular therapy session. A communication protocol can vary among any of the embodiments and alternatives as necessary or desired during a therapy session.

It is intended that the foregoing detailed description be understood as an illustration of selected forms that the invention can take and not as a definition of the invention. It is only the following claims, including all equivalents, which are intended to define the scope of this invention.

What is claimed is:

1. A system for forming an ultrasound image while ablating a tissue, said system comprising:
   a therapy system comprising means for generating a therapy current operative to ablate said tissue, and means for automatically interrupting the generation of therapy current;
   a therapeutic delivery device connected to the therapy system and comprising a therapeutic electrode, the therapeutic electrode being responsive to the therapy current and operative to apply the therapy current to said tissue;
   an ultrasonic imaging system for performing ultrasonic visualization during an automatic interruption of the generation of therapy current, said ultrasonic visualization comprising a detection phase;
   an ultrasound delivery device connected to the ultrasonic imaging system and comprising an ultrasound transducer, the ultrasound transducer being responsive to the ultrasonic imaging system; and
   a communications link connected between the therapy system and the ultrasonic imaging system, the communications link carrying timing signals from at least one of the systems to the other to ensure that at least the detection phase of ultrasonic visualization is performed only during an automatic interruption in the application of therapy current to said tissue.

2. The invention of claim 1, wherein the therapy system and the ultrasonic imaging system are commonly housed in one device.

3. The invention of claim 1, wherein the therapy system and the ultrasonic imaging system are each housed in separate devices.

4. The invention of claim 1, wherein the therapeutic delivery device and the ultrasound delivery device are commonly housed in one delivery device.

5. The invention of claim 1, wherein the therapeutic delivery device and the ultrasound delivery device are each housed in separate delivery devices.

6. The invention of claim 1, wherein the therapy system comprises:
   a current detector;
   a voltage controller responsive to the current detector; and
   a voltage generator responsive to the voltage controller, the voltage generator operative to provide the therapy current operative to ablate said tissue.

7. The invention of claim 1, wherein the tissue is characterized by a temperature, wherein the therapeutic delivery device further comprises a temperature sensor responsive to the temperature of said tissue, and wherein the therapy system further comprises a temperature monitoring system responsive to the sensor.

8. The invention of claim 1, wherein the ultrasonic imaging system comprises:
   a central controller;
   a beam former responsive to the central controller;
   a receiving circuitry responsive to the central controller and to the transducer; and
   a scan converter responsive to the receiving circuitry and the central controller.

9. A method for performing at least a detection phase of an ultrasonic visualization process while ablating a tissue, said method comprising the steps of:
   (a) applying a therapy current to said tissue; then
   (b) automatically interrupting application of therapy current; then
   (c) performing at least a detection phase of an ultrasonic visualization process during step (b); and then
   (d) automatically reapplying the therapy current.

10. The method of claim 9, further comprising the step of using a communication protocol between a therapy system operative to generate the therapy current applied in step (a) and an ultrasonic imaging system operative to perform said at least a detection phase of step (c) to coordinate the timing of steps (a)–(d).

11. The method of claim 9, further comprising the step of using information entered by a user into a therapy system operative to generate the therapy current applied in step (a) and an ultrasonic imaging system operative to perform said at least a detection phase applied in step (c) to coordinate the timing of steps (a)–(d).

12. The method of claim 9, wherein step (a) comprises the step of applying a therapy current to said tissue using a first set of electrical conductors and wherein step (c) comprises the step of performing at least a detection phase of an ultrasonic visualization process during step (b) using a second set of electrical conductors.

13. The method of claim 9, wherein step (c) comprises the step of performing at least a detection phase of an ultrasonic visualization process during step (b) using a phased array ultrasound transducer.

14. The method of claim 9, wherein step (c) comprises the step of performing a plurality of ultrasound detection phases during step (b).

15. A method for performing at least a detection phase of an ultrasonic visualization process while ablating a tissue, said method comprising the steps of:
   (a) performing with an ultrasonic imaging system at least a detection phase of an ultrasonic visualization process; then
   (b) communicating a first signal from the ultrasonic imaging system to a therapy system operative to generate a therapy current, the first signal allowing therapy current to be applied to the tissue and preventing at least the detection phase of the ultrasonic visualization process from being performed during application of therapy current; then
   (c) applying a therapy current to the tissue with the therapy system; and then
   (d) communicating a second signal from the therapy system to the ultrasonic imaging system when a sufficient amount of heat is generated within the tissue for ablation to continue during a time when application of therapy current is interrupted, the second signal interrupting application of therapy current and allowing at least the detection phase of the ultrasonic visualization process to be performed.

16. A method for performing at least a detection phase of an ultrasonic visualization process while ablating a tissue, said method comprising the steps of:
   (a) performing with an ultrasonic imaging system at least a detection phase of an ultrasonic visualization process; then
   (b) communicating a first signal from the ultrasonic imaging system to a therapy system operative to generate a therapy current, the first signal allowing the therapy current to be automatically applied to the tissue and preventing at least the detection phase of the ultrasonic visualization process from being performed during application of therapy current; then
   (c) automatically applying a therapy current to the tissue with the therapy system; and then
   (d) communicating a second signal from the ultrasonic imaging system to the therapy system when a new ultrasound image of the tissue is to be generated, the second signal automatically interrupting application of therapy current and allowing at least the detection phase of the ultrasonic visualization process to be performed.

17. The method of claim 16, wherein step (d) comprises the step of using a minimum frame-rate to determine when a new ultrasound image is to be generated.

18. The method of claim 15 or 16, wherein step (a) comprises the step of performing with an ultrasound imaging system at least a detection phase of an ultrasonic visualization process using a first set of electrical conductors and wherein step (c) comprises the step of applying a therapy current to the tissue with the therapy system using a second set of electrical conductors.

19. The method of claim 15 or 16, wherein step (a) comprises the step of performing at least a detection phase of an ultrasonic visualization process using a phased-array transducer.

20. The method of claim 15 or 16, wherein step (a) comprises the step of performing a plurality of ultrasound detection phases.

21. A method for performing at least a detection phase of an ultrasonic visualization process while ablating a tissue, said method comprising the steps of:
   (a) applying a therapy current to the tissue with a therapy system; then
   (b) communicating a first signal from the therapy system to an ultrasonic imaging system operative to perform at least a detection phase of an ultrasonic visualization process when a sufficient amount of heat is generated within the tissue for ablation to continue during an interruption in application of therapy current, the first signal interrupting application of therapy current and allowing at least an ultrasonic detection phase of an ultrasonic visualization process to be performed; then (c) performing at least the detection phase of the ultrasonic visualization process with the ultrasonic imaging system; and then (d) communicating a second signal from the therapy system to the ultrasonic imaging system when additional heat is needed to maintain a continued ablation of the tissue, the second signal allowing therapy current to be applied to the tissue and preventing at least the detection phase of the ultrasonic visualization process from being performed during application of therapy current.

22. A method for performing at least a detection phase of an ultrasonic visualization process while ablating a tissue, said method comprising the steps of:

(a) applying a therapy current to the tissue with a therapy system; then (b) communicating a signal from the therapy system to an ultrasonic imaging system operative to perform at least a detection phase of an ultrasonic visualization process when a sufficient amount of heat is generated within the tissue for ablation to continue during an interruption of application of therapy current, the signal interrupting application of therapy current and allowing at least a detection phase of an ultrasonic visualization process to be performed; then (c) performing at least the detection phase of the ultrasonic visualization process with the ultrasonic imaging system; and then (d) reapplying the therapy current while continuing at least the detection phase of the ultrasonic visualization process.

23. A method for performing at least a detection phase of an ultrasonic visualization process while ablating a tissue, said method comprising the steps of:

(a) applying a therapy current to the tissue with a therapy system; then (b) communicating a signal from a therapy system to an ultrasonic imaging system operative to perform at least a detection phase of an ultrasonic visualization process when a sufficient amount of heat is generated within the tissue for ablation to continue during an interruption in application of therapy current, the signal providing the ultrasonic imaging system with a selected time period to complete at least a detection phase of an ultrasonic visualization process, interrupting application of therapy current during the performance of at least the detection phase of the ultrasonic visualization process, and allowing at least a detection phase of an ultrasonic visualization process to be performed; then (c) performing at least the detection phase of the ultrasonic visualization process during interruption of therapy current with the ultrasonic imaging system, said at least the detection phase of the ultrasonic visualization process being complete within the selected time period; and then (d) reapplying the therapy current to the tissue.

24. The method of claim 23, wherein the ultrasonic imaging system comprises means for adjusting imaging parameters, and wherein the method further comprises adjusting the imaging parameters to ensure that said at least the detection phase of the ultrasonic visualization process is complete within the selected time period.

25. The method of claim 21, 22, or 23, wherein step (a) comprises the step of applying a therapy current to the tissue with the therapy system using a first set of electrical conductors and wherein step (c) comprises the step of performing with an ultrasound imaging system at least a detection phase of an ultrasonic visualization process using a second set of electrical conductors.

26. The method of claim 21, 22, or 23, wherein step (c) comprises the step of performing at least a detection phase of an ultrasonic visualization process using a phased-array transducer.

27. The method of claim 21, 22, or 23, wherein step (c) comprises the step of performing a plurality of ultrasound detection phases.

28. The method of claim 15, 16, 21, 22, or 23, wherein the ultrasonic imaging system is characterized by a duty cycle, and wherein the method further comprises communicating duty cycle information that varies in accordance with the duty cycle from the ultrasonic imaging system to the therapy system.

29. The method of claim 28, wherein the therapy current is characterized by a magnitude, and wherein the method further comprises altering the magnitude of the therapy current in response to the duty cycle information to ensure that a sufficient amount of heat is generated within the tissue for ablation to continue during interruption of therapy current.

30. The method of claim 28, further comprising the step of repeating steps (a)–(d) to achieve a cumulative therapy time in response to the duty cycle information.

31. The method of claim 15, 16, 21, 22, or 23, wherein the therapy current has a magnitude, and wherein the method further comprises the step of monitoring a time-average of the square of the therapy current and varying the magnitude of the therapy current to ensure that a sufficient amount of heat is generated within the tissue for ablation to continue during interruption of therapy current.

32. The method of claim 15, 16, 21, 22, or 23, wherein the method comprises the further steps of monitoring a time-average of the square of the therapy current and repeating steps (a)–(d) a plurality of times based on the time-average of the square of the therapy current to ensure that a sufficient amount of heat is generated within the tissue for ablation.

33. The method of claim 15, 16, 21, 22, or 23, wherein the tissue has a temperature, and wherein the method further comprises the step of repeating steps (a)–(d) a plurality of times based on the tissue temperature to ensure that a sufficient amount of heat is generated within the tissue for ablation.

34. The invention of claim 1, wherein a first set of electrical conductors couple said therapeutic electrode with said therapy system and a second set of electrical conductors couple said ultrasound transducer with said ultrasonic imaging system.

35. The invention of claim 1, wherein said ultrasound transducer comprises a phased-array transducer.

* * * * *